United States Patent
Petit-Clair et al.

(10) Patent No.: US 10,946,370 B2
(45) Date of Patent: Mar. 16, 2021

(54) METHOD FOR PREPARING A SELECTIVE HYDROGENATION CATALYST

(71) Applicant: IFP Energies nouvelles, Rueil-Malmaison (FR)

(72) Inventors: Carine Petit-Clair, Jardin (FR); Priscilla Avenier, Grenoble (FR); Michel Martin, Lyons (FR); Malika Boualleg, Villeurbanne (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 145 days.

(21) Appl. No.: 16/305,772

(22) PCT Filed: Apr. 24, 2017

(86) PCT No.: PCT/EP2017/059640
§ 371 (c)(1),
(2) Date: Nov. 29, 2018

(87) PCT Pub. No.: WO2017/207168
PCT Pub. Date: Dec. 7, 2017

(65) Prior Publication Data
US 2020/0254436 A1    Aug. 13, 2020

(30) Foreign Application Priority Data
May 30, 2016  (FR) ..................... 1654833

(51) Int. Cl.
*B01J 37/02*   (2006.01)
*B01J 23/44*   (2006.01)
(Continued)

(52) U.S. Cl.
CPC ........... *B01J 37/0213* (2013.01); *B01J 6/001* (2013.01); *B01J 23/44* (2013.01); *B01J 35/1061* (2013.01)

(58) Field of Classification Search
CPC .... B01J 23/44; B01J 37/0213; B01J 35/1061; B01J 6/001; B01J 21/04; B01J 21/08; B01J 21/12
See application file for complete search history.

(56) References Cited

U.S. PATENT DOCUMENTS 4,230,897 A * 10/1980 Cosyns .................... B01J 23/44
                                                            585/260
4,484,015 A * 11/1984 Johnson ................... B01J 23/50
                                                            585/259
(Continued)

FOREIGN PATENT DOCUMENTS

FR  2922784 A1   5/2009
FR  2968578 A1   6/2012
(Continued)

OTHER PUBLICATIONS

International Search Report PCT/EP2017/059640 dated Dec. 6, 2017 (pp. 1-16).

*Primary Examiner* — Cam N. Nguyen
(74) *Attorney, Agent, or Firm* — Millen, White, Zelano & Branigan, PC; Ryan Pool

(57) ABSTRACT

A process for the preparation of a catalyst comprising palladium, a porous support with a specific surface area in the range 140 to 250 m²/g, said catalyst being prepared by a process comprising the following steps:
a) preparing a colloidal solution of palladium oxide or palladium hydroxide in an aqueous phase;
b) adding said solution obtained from step a) to said porous support at a flow rate in the range 1 to 20 litre(s)/hour; said porous support being contained in a rotary impregnation device functioning at a rotational speed in the range 10 to 20 rpm;
c) optionally, submitting the impregnated porous support obtained from step b) to a maturation;
(Continued)

d) drying the catalyst precursor obtained from step b) or c);
e) calcining the catalyst precursor obtained from step d).

18 Claims, 1 Drawing Sheet

(51) Int. Cl.
  *B01J 35/10* (2006.01)
  *B01J 21/04* (2006.01)
  *B01J 21/08* (2006.01)
  *B01J 21/12* (2006.01)
  *B01J 6/00* (2006.01)

(56) References Cited

U.S. PATENT DOCUMENTS

| | | | |
|---|---|---|---|
| 4,493,906 A * | 1/1985 | Couvillion | B01J 23/72 502/346 |
| 4,940,687 A * | 7/1990 | Liu | B01J 21/04 502/325 |
| 5,583,274 A * | 12/1996 | Cheung | C07C 5/09 585/261 |
| 5,648,576 A * | 7/1997 | Nguyen Than | B01J 23/44 585/260 |
| 5,889,187 A * | 3/1999 | Nguyen Than | B01J 23/44 585/260 |
| 6,054,409 A * | 4/2000 | Nguyen Thanh | B01J 23/44 502/328 |
| 6,350,717 B1 * | 2/2002 | Frenzel | B01J 23/44 502/327 |
| 8,637,719 B2 | 1/2014 | Fischer | |
| 8,841,231 B2 | 9/2014 | Fecant | |
| 9,695,095 B2 * | 7/2017 | Dubreuil | B01J 23/44 |
| 10,099,205 B2 | 10/2018 | Cabiac | |
| 2010/0125158 A1* | 5/2010 | Negiz | C07C 5/05 585/260 |
| 2010/0197488 A1* | 8/2010 | Hagemeyer | C07C 67/055 502/242 |
| 2018/0147563 A1* | 5/2018 | Boualleg | B01J 35/0066 |
| 2018/0147564 A1* | 5/2018 | Boualleg | B01J 21/08 |
| 2019/0126246 A1* | 5/2019 | Petit-Clair | B01J 35/023 |

FOREIGN PATENT DOCUMENTS

| | | |
|---|---|---|
| FR | 2991197 A1 | 12/2013 |
| FR | 2993795 A1 | 1/2014 |

* cited by examiner

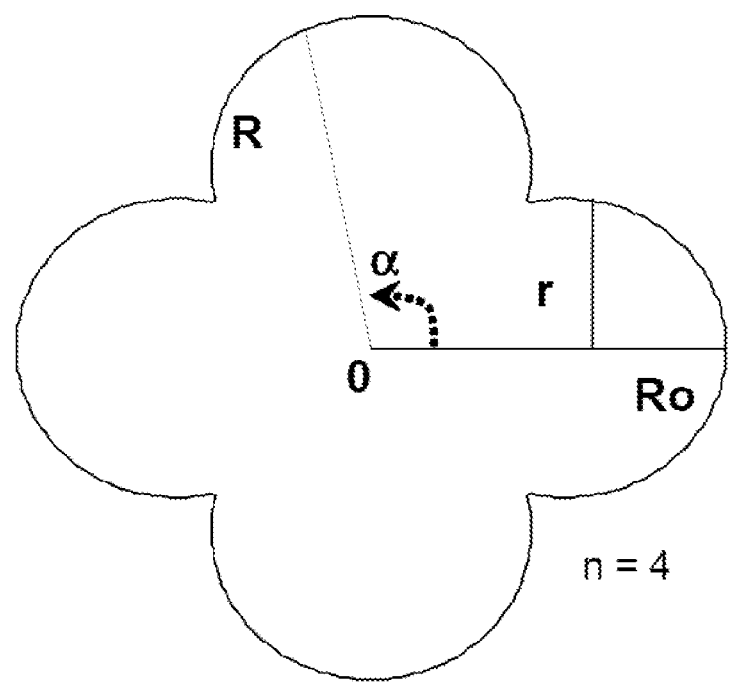

METHOD FOR PREPARING A SELECTIVE HYDROGENATION CATALYST

TECHNICAL FIELD

The selective hydrogenation process can be used to transform the polyunsaturated compounds of oil cuts by conversion of the most unsaturated compounds into the corresponding alkenes, avoiding complete saturation and thus the formation of the corresponding alkanes.

The aim of the invention is to propose a process for the preparation of a catalyst with improved performances and a process for the selective hydrogenation of unsaturated hydrocarbon compounds present in the hydrocarbon cuts, preferably cuts obtained from steam cracking or from catalytic cracking.

PRIOR ART

Catalysts for the selective hydrogenation of such cuts are often based on palladium, in the form of small metallic particles deposited on a support which may be a refractory oxide. The palladium content and the size of the particles of palladium are some of the criteria which are important as regards the activity and selectivity of the catalysts.

The macroscopic distribution of the metallic particles in the support also constitutes an important criterion, principally in the context of rapid and consecutive reactions such as selective hydrogenations. Generally, these elements have to be located in a crust at the periphery of the support in order to avoid problems with intragranular material transfer which could lead to defective activity and a loss of selectivity. As an example, the document US2006/025302 describes a catalyst for the selective hydrogenation of acetylene and diolefins, comprising palladium distributed in a manner such that 90% of the palladium is introduced into the catalyst in a crust of less than 250 μm.

In general, the active phase of palladium is deposited on the support in accordance with any of the techniques known to the person skilled in the art, for example by dry impregnation or moist techniques.

The selective hydrogenation catalysts are very often shaped using methods which are known to the person skilled in the art, and in particular by mixing-extrusion, pelletization, granulation, or oil-drop methods. The selective hydrogenation catalysts may thus be in the form of beads, cylinders, wheels, hollow cylinders, honeycombs or any other geometric form known to the person skilled in the art. However, any advantages brought about by the shape of the catalyst support as regards the dispersion of the metallic particles on the catalyst support, and thus on its catalytic activity, have not been differentiated. For the same structural and textural properties of the selective hydrogenation catalyst, the shape of the selective hydrogenation catalyst thus does not, a priori, have an effect on the performances in terms of catalytic activity.

Completely surprisingly, the Applicant has discovered that catalysts comprising palladium and a porous support with a precise specific surface area, prepared using a particular technique for impregnating palladium onto said porous support, means that the distribution of the metallic particles at the surface of said catalyst can be improved, and that improved catalytic activity performances are obtained, in the sense that their catalytic activity is significantly higher than that of catalysts obtained by conventional preparation methods. The preparation process in accordance with the invention can be used to prepare catalysts with a very thin crust thickness.

A catalyst obtained using such a preparation process can provide a higher available external surface area and can provide more superficial impregnation of the support, as well as providing an improved accessibility of the feed to the active phase.

SUBJECT MATTER OF THE INVENTION

The invention concerns a process for the preparation of a catalyst comprising palladium, a porous support comprising at least one refractory oxide selected from the group constituted by silica, alumina and silica-alumina, said porous support comprising a specific surface area in the range 140 to 250 $m^2/g$, in which at least 80% by weight of the palladium is distributed in a crust at the periphery of said support, the thickness of said crust being in the range 20 to 100 μm, said process comprising the following steps:

a) preparing a colloidal solution of palladium oxide or palladium hydroxide in an aqueous phase;
b) adding said solution obtained from step a) to said porous support at a flow rate in the range 1 to 20 litre(s)/hour; said porous support being contained in a rotary impregnation device functioning at a rotational speed in the range 10 to 20 rpm;
c) optionally, submitting the impregnated porous support obtained from step b) to a maturation in order to obtain a catalyst precursor;
d) drying the catalyst precursor obtained from step b) or c) at a temperature in the range 70° C. to 200° C.;
e) calcining the catalyst precursor obtained from step d) at a temperature in the range 300° C. to 500° C.

In one embodiment of the invention, said porous support is in the form of a bead.

In another embodiment of the invention, said porous support is in the form of an extrudate.

Advantageously, said porous support is in the form of an extrudate with a length h in the range 2 to 10 mm.

Preferably, said porous support comprises a section comprising at least three lobes.

More preferably, the number of lobes of the extrudate, n, is selected from the group constituted by the integer values 3, 4, 5, 6, 7, 8, 9 and 10.

Yet more preferably, the number of lobes, n, is selected from the group constituted by the integer values 3 and 4.

In another embodiment, the extrudate is in the form of a cylinder.

Advantageously, the palladium content in the catalyst is in the range 0.01% to 2% by weight with respect to the total catalyst weight.

Preferably, said catalyst further comprises silver at a content in the range 0.02% to 3% by weight of silver with respect to the total catalyst weight.

Advantageously, the metallic dispersion D of the palladium is in the range 15% to 70%.

Advantageously, the support has a pore diameter in the range 2 to 50 nm.

In a particular embodiment, a maturation step c) is carried out for a period in the range 0.5 to 40 hours.

In a particular embodiment, said dried catalyst obtained from step e) undergoes a reduction treatment by contact with a reducing gas at a temperature in the range 80° C. to 180° C.

Advantageously, the rotary impregnation device of step b) is a revolving drum.

DETAILED DESCRIPTION OF THE INVENTION

Hereinbelow, the groups of the chemical elements are provided in accordance with the CAS classification (CRC Handbook of Chemistry and Physics, published by CRC press, editor-in-chief D. R. Lide, $81^{st}$ edition, 2000-2001). As an example, group VIIIB in the CAS classification corresponds to metals from columns 8, 9 and 10 of the new IUPAC classification.

The textural and structural properties of the support and catalyst described below are determined using characterization methods which are known to the person skilled in the art. The total pore volume and pore distribution are determined in the present invention by mercury porosimetry (cf. Rouquerol F.; Rouquerol J.; Singh K. "Adsorption by Powders & Porous Solids: Principle, methodology and applications", Academic Press, 1999). More particularly, the total pore volume is measured by mercury porosimetry in accordance with ASTM standard D4284-92 with a wetting angle of 140°, for example with the aid of an Autopore III™ model instrument from Micromeritics™. The specific surface area is determined in the present invention by the BET method described in the same reference work as for the mercury porosimetry, and more particularly in accordance with ASTM standard D3663-03.

1. Definitions

Metallic Dispersion of Particles (D)

The particle dispersion is a dimensionless quantity, often expressed as a percentage. The dispersion becomes larger as the particles become smaller. It is defined in the publication by R. Van Hardeveld and F. Hartog, "*The statistics of surface atoms and surface sites on metal crystals*", Surface Science 15, 1969, 189-230.

Definition of the Coefficient R

The distribution profiles for the elements in the grains of catalyst are obtained using a Castaing microprobe. At least 30 analysis points are recorded along the diameter of the bead or extrudate, with about ten points on the crust of an active element (in this case palladium) and about ten at the central point of the grain. This produces the distribution profile c(x) for $x \in [-r; +r]$ with c being the local concentration of the element, r the radius of the bead or extrudate and x the position of the analysis point along the diameter of the grain with respect to the centre of that grain.

The distribution of the elements is characterized by a dimensionless coefficient R weighting the local concentration by a weight which increases as a function of the position on the diameter. By definition:

$$R = \int_{-r}^{r} c(x) x^2 dx / \frac{r^2}{3} \int_{-r}^{r} c(x) dx$$

Thus, an element with a uniform concentration has a coefficient R equal to 1, an element deposited in a domed profile (concentration at the core higher than the concentration at the edges of the support) has a coefficient of more than 1 and an element distributed as a crust (concentration at the edges higher than the concentration at the core of the support) has a coefficient of less than 1. Analysis by Castaing microprobe provides values for the concentrations at a finite number of values for x, and so R is then evaluated numerically using integration methods which are well known to the person skilled in the art. Preferably, R is determined using the trapezium rule.

The distribution of the alkali element is defined as homogeneous when the distribution coefficient R defined above is in the range 0.8 to 1.2.

The distribution of the alkaline-earth element is defined as homogeneous when the distribution coefficient R defined above is in the range 0.8 to 1.2.

Definition of Palladium Crust Thickness

In order to analyse the distribution of the metallic phase on the support, a crust thickness is measured by Castaing microprobe (or electronic microprobe microanalysis). The instrument used is a CAMECA® SX100, equipped with four crystal monochromators in order to analyse four elements simultaneously. The technique for analysis using the Castaing microprobe consists of the detection of X-rays emitted by a solid after excitation of its elements using a high energy electron beam. For the purposes of this characterization, the grains of catalyst are embedded in epoxy resin blocks. These blocks are polished until the section with the diameter of the beads or extrudates is obtained, then metallized by depositing carbon in a metallic evaporator. The electronic probe is scanned along the diameter of five beads or extrudates in order to obtain the mean distribution profile of the constituent elements of the solids.

When the palladium is distributed in the form of a crust, its local concentration generally reduces steadily when it is measured, starting from the edge of the catalytic grain towards the interior. A distance from the grain edge at which the local palladium content becomes zero often cannot be determined with reproducible precision. In order to measure a crust thickness which is significant for the majority of the palladium particles, the crust thickness is defined as the distance to the grain edge containing 80% by weight of the palladium. It is defined in the publication by L. Sorbier et al. "*Measurement of palladium crust thickness on catalyst by EPMA*" Materials Science and Engineering 32 (2012). In order to measure a crust thickness which is significant for the majority of palladium particles, the crust thickness may alternatively be defined as the distance to the grain edge containing 80% by weight of the palladium. Starting from the distribution profile obtained using the Castaing microprobe (c(x)), it is possible to calculate the cumulative quantity Q(y) of palladium in the grain as a function of the distance y to the edge of a grain with radius r.

For a bead:

$$Q(y) = \int_{-r}^{-r+y} c(x) 4\pi \cdot x^2 dx + \int_{r-y}^{r} c(x) 4\pi \cdot x^2 dx$$

For an extrudate:

$$Q(y) = \int_{-r}^{-r+y} c(x) 2\pi \cdot x dx + \int_{r-y}^{r} c(x) 2\pi \cdot x dx$$

where
r: radius of grain;
y: distance to edge of grain;
x: integration variable (position on the profile).

It is assumed that the concentration profile follows the diameter from x=−r to x=+r (x=0 being the centre).

Q(r) thus corresponds to the total quantity of the element in the grain. The following equation is then solved numerically for y:

$$\frac{Q(y)}{Q(r)} = 0.8$$

where c is a strictly positive function, Q is thus a strictly increasing function and this equation has a unique solution which is the thickness of the crust.

Proximity Ratio PR

In one embodiment of the invention, the catalyst also comprises silver (Ag). The palladium (Pd)-silver (Ag) catalysts are characterized by Castaing microprobe. This analysis provides the local concentration by weight of the metals Pd, Ag.

For a catalyst, this analysis can be used to determine the relative distribution of the two metals along the catalytic grain by integration of a succession of XRF analyses at a distance y at the edge of the grain. The formula which can be used to estimate the proximity of the two metals is as follows:

$$\text{Proximity ratio} = RP(y) = \frac{Q(y)Pd/Q(r)Pd}{Q(y)Ag/Q(r)Ag}$$

where:

$Q(y)$ Pd=sum of concentrations of palladium between the edge of the grain and a distance y from the edge of the catalytic grain (% by wt)

$Q(y)$ Ag=sum of concentrations of silver between the edge of the grain and a distance y from the edge of the catalytic grain (% by wt)

$Q(r)$ Pd=total palladium content in the catalytic grain (% by wt)

$Q(r)$ Ag=total silver content in the catalytic grain (% by wt).

This therefore defines a proximity criterion which takes into account the relative location of the two metals in the support. The latter, determined by microprobe, represents the weight ratio at any point y of the support of the added metallic elements, in our case Pd and Ag. The proximity ratio of a catalyst containing locally uniformly distributed metals will be 1.

In the catalyst in accordance with the invention, the proximity ratio PR is in the range 0.5 to 2, preferably in the range 0.8 to 1.4.

1. Catalyst Preparation Process

The catalyst prepared by the preparation process in accordance with the invention is a catalyst comprising palladium, a porous support comprising at least one refractory oxide selected from the group constituted by silica, alumina and silica-alumina, said porous support comprising a specific surface area in the range 140 to 250 m$^2$/g, in which at least 80% by weight of the palladium is distributed in a crust at the periphery of said support, the thickness of said crust being in the range 20 to 100 µm, preferably in the range 25 to 90 µm, said catalyst being prepared by a process comprising at least the following steps:

a) preparing a colloidal solution of palladium oxide or palladium hydroxide in an aqueous phase;

b) adding said solution obtained from step a) to said porous support at a flow rate in the range 1 to 20 litre(s)/hour; said porous support being contained in a rotary impregnation device functioning at a rotational speed in the range 10 to 20 rpm;

c) optionally, submitting the impregnated porous support obtained from step b) to a maturation in order to obtain a catalyst precursor;

d) drying the catalyst precursor obtained from step b) or c) at a temperature in the range 70° C. to 200° C.;

e) calcining the catalyst precursor obtained from step d) at a temperature in the range 300° C. to 500° C.

The various steps of the process for forming the catalyst in accordance with the invention are explained in detail below.

a) Preparation of a Colloidal Suspension of Palladium Oxide or Palladium Hydroxide in an Aqueous Phase The colloidal suspension is generally obtained by hydrolysis of the palladium cation in an aqueous medium, which results in the formation of particles of palladium oxide or hydroxide in suspension.

The aqueous solution of alkali hydroxides or alkaline-earth hydroxides is generally selected from the group constituted by aqueous solutions of sodium hydroxide, aqueous solutions of magnesium hydroxide. Preferably, the aqueous solution is by preference an aqueous solution of sodium hydroxide.

Typically, the aqueous solution comprising at least one precursor salt of palladium [hereinafter also termed solution (II)] is supplied to a suitable apparatus, followed by the aqueous solution comprising at least one alkali hydroxide or alkaline-earth hydroxide [hereinafter also termed solution (I)]. Alternatively, the solutions (I) and (II) may be poured into the apparatus simultaneously. Preferably, the aqueous solution (II) is poured into the apparatus, followed by the aqueous solution (I).

The palladium precursor salt is generally selected from the group constituted by palladium chloride, palladium nitrate and palladium sulphate. Highly preferably, the precursor salt of palladium is palladium nitrate.

The colloidal suspension generally remains in the apparatus for a dwell time in the range 0 to 20 hours.

The concentrations of the solutions (I) and (II) are generally selected in order to obtain a pH of the colloidal suspension in the range 1.0 to 3.5. Thus, the pH of the colloidal suspension may be modified during this dwell time by adding quantities of acid or base compatible with the stability of the colloidal suspension.

In general, the preparation temperature is in the range 5° C. to 40° C., preferably in the range 15° C. to 35° C.

The concentration of palladium is preferably in the range 5 to 150 millimoles per litre (mmol/L), more preferably in the range 8 to 80 millimoles per litre.

b) Depositing the Colloidal Suspension Prepared in Step a) by Impregnation onto a Support The colloidal suspension prepared in step a) is then impregnated onto a support.

The porous support comprises at least one refractory oxide selected from the group constituted by silica, alumina and silica-alumina. Preferably, the porous support is alumina.

The porous support may either be in the form of a bead or in the form of an extrudate. The term "extruded support" means a support comprising a length h and an equivalent diameter Deq in which the length h is greater than the equivalent diameter Deq. Preferably, the extrudate comprises a length h in the range 2 to 10 mm, preferably in the range 2 to 8 mm, and more preferably in the range 3 to 6 mm.

Preferably, the extrudate is selected from cylinders and extrudates comprising a section comprising at least three lobes.

In a preferred embodiment of the invention, the extrudate comprises a section comprising at least three lobes.

When the extrudate comprises a section comprising at least three lobes, the section of the extrudate may be characterized by a radius R which satisfies equation (1):

$$R = \cos\theta \cdot (R_o - r) + \sqrt{\cos^2\theta \cdot (R_o - r)^2 - R_o \cdot (R_o - 2 \cdot r)} \quad (1)$$

$$\text{where } \theta = \alpha - k \cdot \frac{2 \cdot \pi}{n} \text{ and } k = Int\left(\frac{\left|\alpha + \frac{\pi}{2}\right|}{\frac{2 \cdot \pi}{n}}\right)$$

$$\text{and } \alpha \in [0, 2\pi]$$

where $R_o$ represents the maximum distance between the centre of the extrudate and the wall of the extrudate, R represents the distance between the centre of the extrudate and the wall of the extrudate for an angle a, r represents the radius of a lobe of the extrudate, n corresponds to the number of lobes of the extrudate, and the function Int( ) represents the integer portion of the ratio $$\left(\frac{\left|\alpha + \frac{\pi}{2}\right|}{\frac{2 \cdot \pi}{n}}\right) \text{ and } \left|\alpha + \frac{\pi}{2}\right|$$

represents the absolute value of the sum $$\alpha + \frac{\pi}{2}.$$

In accordance with the present invention, the function "Int( )" means the integer portion of the ratio $$\left(\frac{\left|\alpha + \frac{\pi}{2}\right|}{\frac{2 \cdot \pi}{n}}\right).$$

Thus, by way of illustration, applying the function Int( ) for a ratio equal to 1.8 corresponds to the integer value 1, i.e. Int(1.8)=1, and applying the function Int( ) for a ratio equal to 2.1 corresponds to the integer value 2, i.e. Int(2.1)=2.

Advantageously, in this particular embodiment of the invention, the number of lobes of extrudate n is selected from the group constituted by the integer values 3, 4, 5, 6, 7, 8, 9 and 10; preferably, the number of lobes n is selected from the group constituted by the integer values 3, 4, 5 and 6; more preferably, the number of lobes is selected from the group constituted by the integer values 3 and 4; highly preferably, the number of lobes n is 3.

For the purposes of greater clarity in the application of equation (1) in accordance with the invention, FIG. 1 shows an illustrative and non-limiting diagram of a section of an extrudate which shows all of the parameters $R_o$, R, r and a, n being the number of lobes of the extrudate. The section of the extrudate corresponds to a section of the extrudate in a plane perpendicular to the direction of extrusion. Referring to FIG. 1, the section of the extrudate comprises four lobes.

The processes for the production of supported extrudates which are known to the person skilled in the art usually give rise to imperfections in the shape linked to the mechanics of the phases which are present, which could cause a difference between the measurable value R ($R_{mes}$) and the value R defined by the equation (1). The measurable value R ($R_{mes}$) linked to the value R defined by equation (1) of the present invention is advantageously in the range R−15% R to R+15% R, preferably in the range R−10% R to R+10% R, more preferably in the range R−5% R to R+5% R, yet more preferably in the range R−3% R to R+3% R.

In accordance with the invention, the specific surface area of the porous support is in the range 140 to 250 m²/g, preferably in the range 165 to 250 m²/g, more preferably in the range 170 to 220 m²/g and yet more preferably in the range 175 to 210 m²/g.

The pore volume of the support is generally in the range 0.1 to 1.5 cm³/g, preferably in the range 0.2 to 1 cm³/g.

Preferably, the support for the selective hydrogenation catalyst is purely mesoporous, i.e. it has a pore diameter in the range 2 to 50 nm, preferably in the range 5 to 30 nm and yet more preferably in the range 8 to 20 nm. In this embodiment, the catalyst support thus comprises neither micropores (<2 nm) nor macropores (>50 nm).

The support may optionally comprise sulphur. The sulphur may originate from at least one of the precursors for the synthesis of the alumina support, in particular aluminium sulphate. A residual quantity of sulphur is contained in the final support, which is a function of the pH for precipitation of the alumina gel. The sulphur content comprised in the support may be in the range 0.0050% to 0.25% by weight with respect to the total catalyst weight, preferably in the range 0.0075% to 0.20% by weight.

The support may optionally undergo a series of treatments before the impregnation step, such as calcining or hydration treatments. The support may also already comprise one or more metallic elements before impregnation of the colloidal suspension. Metallic elements may also be introduced into the colloidal suspension. These metallic elements may be introduced either by conventional techniques, or by using the process in accordance with the present invention.

In accordance with the invention, the colloidal suspension is poured onto the support. This procedure is carried out in a rotary impregnation device such as an impregnation drum, in a continuous manner, i.e. the step for the preparation of the colloidal suspension precedes the step for impregnation onto the support and that the main part of the colloidal suspension is sent to the impregnation step continuously, after adjusting the dwell time of the colloidal suspension in step b).

The rotary impregnation device used is preferably a conventional impregnation drum the vessel of which may be placed under reduced pressure (approximately 20 mm Hg) or be flushed with gas (nitrogen).

The rotary impregnation device is equipped with a double jacket in which a coolant fluid moves via a temperature controller. Thus, it is possible to regulate a wall temperature in the impregnator and a drying time. In a preferred embodiment, the impregnation temperature is in the range 40° C. to 90° C., preferably in the range 50° C. to 70° C.

In accordance with the invention, the rotary impregnation device in which the support, with a specific surface area in the range 140 to 250 m²/g, has been placed, operates at a rotational speed in the range 4 to 20 rpm. Above 20 rpm, the crust of palladium obtained on the support is too thin, i.e. below 20 μm, and a portion of the palladium is not impregnated onto the support. If the rotation of the drum is too low, i.e. less than 4 rpm, the crust of palladium obtained on the support may exceed 100 μm in thickness, and the dispersion of palladium on the support is not satisfactory, i.e. less than 15%.

In accordance with the invention, the flow rate at which the colloidal solution obtained from step a) is added to the porous support is in the range 1 to 20 litre(s) per hour. Above 20 litres per hour, the palladium crust obtained is too thick, i.e. above 100 μm, and the dispersion of the palladium is not satisfactory, i.e. below 15%.

As an example, a process in which the colloidal solution is poured into a tank which continuously overflows into a revolving drum comprising the support to be impregnated may be mentioned in respect of a continuous process.

c) Maturation of Support Impregnated during Step b) for a Period in the Range 0.5 to 40 Hours (Optional Step)

After impregnation, the impregnated support may be matured in the moist state for 0.5 to 40 h, preferably for 1 to 30 h.

d) Drying the Catalyst Precursor Obtained from Step b) or c)

The catalyst precursor is generally dried in order to eliminate all or a portion of the water introduced during impregnation, preferably at a temperature in the range 50° C. to 250° C., more preferably in the range 70° C. to 200° C. The drying period is in the range 0.5 h to 20 h.

Drying is generally carried out in air from the combustion of a hydrocarbon, preferably methane, or in heated air comprising between 0 and 80 grams of water per kilogram of combustion air, an oxygen content in the range 5% to 25% by volume and a carbon dioxide content in the range 0 to 10% by volume.

e) Calcining the Dried Catalyst Obtained in Step d) in Combustion Air

After drying, the catalyst is generally calcined in combustion air, preferably air from the combustion of methane comprising between 40 and 80 grams of water per kg of combustion air, an oxygen content in the range 5% to 15% by volume and a $CO_2$ content in the range 4% to 10% by volume. The calcining temperature is generally in the range 250° C. to 900° C., preferably in the range from approximately 300° C. to approximately 500° C. The calcining period is generally in the range 0.5 h to 5 h.

f) Reduction of Supported Oxide Obtained from Step e), Preferably Using Gaseous Hydrogen (Optional Step)

The catalyst is generally reduced. This step is preferably carried out in the presence of a reducing gas, either in situ, i.e. in the reactor in which the catalytic transformation is carried out, or ex situ. Preferably, this step is carried out at a temperature in the range 80° C. to 180° C., more preferably in the range 100° C. to 160° C.

The reduction is carried out in the presence of a reducing gas comprising between 25% by volume and 100% by volume of hydrogen, preferably 100% by volume of hydrogen. The hydrogen is optionally supplemented by a gas which is inert to reduction, preferably argon, nitrogen or methane.

The reduction generally comprises a temperature rise phase followed by a constant temperature stage.

The duration of the constant temperature stage for reduction is generally in the range 1 to 10 hours, preferably in the range 2 to 8 hours.

The hourly space velocity (HSV) is generally in the range 150 to 3000, preferably in the range 300 to 1500 litres of reducing gas per hour and per litre of catalyst.

In a variation, the catalyst may contain one or more promoter metals, in particular silver. The promoter metal or metals may be introduced during the preparation of the support, onto the support which has already been shaped, during step a) or at the end of steps b), c), d), e) or f).

In a particular embodiment of the invention, the catalyst furthermore comprises silver. The silver may be introduced during the preparation of the support, onto the support which has already been shaped, during step a) or at the end of steps b), c), d), e) or f).

The silver may advantageously be deposited onto the support using any method known to the person skilled in the art, preferably by impregnation of said support with at least one solution containing at least one precursor of silver, and preferably by dry impregnation or excess impregnation. This solution contains at least one silver precursor in the concentration required to obtain, on the final catalyst, a silver content in the range 0.02% to 3% by weight of silver with respect to the total weight of catalyst, preferably in the range 0.05% to 0.3% by weight.

In the embodiment in which the catalyst additionally comprises silver, at least 80% by weight of the silver is distributed in a crust at the periphery of the support, the thickness of said crust being in the range 20 to 100 μm, preferably in the range 25 to 90 μm, the local silver content at each point along the grain diameter varying in the same manner as the local palladium content.

The catalyst obtained by the process in accordance with the invention may comprise at least one metal selected from the group constituted by alkalis and alkaline-earths.

The alkali metal is generally selected from the group constituted by lithium, sodium, potassium, rubidium and caesium, preferably by lithium, sodium and potassium, and highly preferably by sodium and potassium. More preferably, the alkali metal is sodium.

The alkaline-earth metal is generally selected from the group constituted by magnesium, calcium, strontium and barium, preferably by magnesium and calcium, and highly preferably magnesium.

When it is present, the alkali metal is distributed in a homogeneous manner through the support, with a coefficient R in the range 0.8 to 1.2.

When it is present, the alkaline-earth metal is distributed in a homogeneous manner through the support, with a coefficient R in the range 0.8 to 1.2.

The catalyst obtained by the process in accordance with the invention has a metallic dispersion (D) which is in the range 15% to 70%, preferably in the range 20% to 70%, and more preferably in the range 25% to 60%.

The catalyst obtained by the process in accordance with the invention has a palladium content in the range 0.01% to 2% by weight of palladium, preferably in the range 0.05% to 1% by weight with respect to the total catalyst weight.

Use of the Catalyst

The catalyst in accordance with the invention may be used in processes which involve a transformation of organic compounds. Thus, the catalyst in accordance with the invention may be used in processes comprising reactions for the hydrogenation of compounds comprising aromatic, ketone, aldehyde, acidic or nitro functions, the hydrogenation of carbon monoxide to C1-C6 alcohols, to methanol or to dimethyl ether, isomerization or hydroisomerization reactions, hydrogenolysis reactions, and in general reactions which involve breaking or forming carbon-carbon bonds.

The operating conditions generally used for these reactions are as follows: a temperature in the range 0° C. to 500° C., preferably in the range 25° C. to 350° C., a pressure in the range 0.1 to 20 MPa, preferably in the range 0.1 to 10 MPa, an hourly space velocity (HSV) in the range 0.1 to 50 $h^{-1}$, preferably in the range 0.5 to 20 $h^{-1}$ for a liquid feed; and in the range 500 to 30000 $h^{-1}$, preferably in the range 500 to 15000 $h^{-1}$ for a gaseous feed. When hydrogen is present, the molar ratio of hydrogen to feed is in the range 1 to 500 litres per litre, preferably in the range 10 to 150 litres per litre.

Use of the catalyst in accordance with the invention and the conditions for its use must be adapted by the user to the reaction and to the technology employed.

The catalyst in accordance with the invention may also be used in reactions for the hydrogenation of compounds comprising acetylenic, dienic or olefinic functions.

The invention also concerns the process for selective hydrogenation by bringing a feed into contact with the catalyst in accordance with the invention or the catalyst prepared in accordance with the invention, said feed being selected from the group constituted by steam cracked C3 cuts, steam cracked C4 cuts, steam cracked C5 cuts and steam cracked gasolines, also known as pyrolysis gasolines.

In accordance with a preferred application, the catalysts in accordance with the invention are employed in reactions for the selective hydrogenation of polyunsaturated hydrocarbon cuts obtained from steam cracking and/or catalytic cracking, preferably polyunsaturated hydrocarbon cuts obtained from steam cracking.

Hydrogenation of C3 to C5 Cuts

Processes for the conversion of hydrocarbons such as steam cracking or catalytic cracking are operated at high temperatures and produce a wide variety of unsaturated molecules such as ethylene, propylene, linear butenes, isobutene, pentenes as well as unsaturated molecules containing up to about 15 carbon atoms.

At the same time, polyunsaturated compounds are also formed: acetylene, propadiene and methylacetylene (or propyne), 1,2- and 1,3-butadiene, vinylacetylene and ethylacetylene, and other polyunsaturated compounds with a boiling point corresponding to the C5+ gasoline fraction.

All of these polyunsaturated compounds have to be eliminated in order to allow these various cuts to be used in petrochemicals processes such as polymerization units.

Thus, for example, the C3 steam cracking cut may have the following average composition: of the order of 90% by weight of propylene, of the order of 3% to 8% by weight of propadiene and methylacetylene, the rest essentially being propane. In certain C3 cuts, between 0.1% and 2% by weight of C2 and C4 compounds may also be present. The specifications concerning the concentrations of these polyunsaturated compounds for the petrochemicals and polymerization units are very low: 20-30 ppm by weight of MAPD (MethylAcetylene and PropaDiene) for chemical quality propylene, and less than 10 ppm by weight or even up to 1 ppm by weight for "polymerization" quality.

A C4 steam cracking cut has the following average molar composition, for example: 1% of butane, 46.5% of butene, 51% of butadiene, 1.3% of VinylAcetylene (VAC) and 0.2% of butyne. In certain C4 cuts, between 0.1% and 2% by weight of C3 and C5 compounds may also be present. Here again, the specifications are severe: diolefins content strictly less than 10 ppm by weight for a C4 cut which will be used in petrochemicals or polymerization.

A C5 steam cracked cut has the following average composition by weight, for example: 21% of pentanes, 45% of pentenes, 34% of pentadienes.

The selective hydrogenation process has been gaining momentum in the elimination of polyunsaturated compounds from the cited C3 to C5 oil cuts, because this process can be used to convert the most unsaturated compounds into the corresponding alkenes, avoiding complete saturation and thus the formation of the corresponding alkanes.

Selective hydrogenation may be carried out in the gas or liquid phase, preferably in the liquid phase. In fact, a liquid phase reaction may be used to reduce energy costs and increase the catalyst cycle time.

For a liquid phase reaction, the pressure is generally in the range 1 to 3 MPa, the temperature is in the range 2° C. to 50° C. and the hydrogen/(polyunsaturated compounds to be hydrogenated) molar ratio is in the range 0.1 to 4, preferably in the range 1 to 2.

For a gas phase hydrogenation reaction, the pressure is generally in the range 1 to 3 MPa, the temperature is in the range 40° C. to 120° C. and the hydrogen/(polyunsaturated compounds to be hydrogenated) molar ratio is in the range 0.1 to 4, preferably in the range 1 to 2.

Hydrogenation of Steam Cracked Gasolines

Steam cracking principally produces ethylene, propylene, a C4 cut as well as steam cracked gasoline, which is also known as pyrolysis gasoline.

In accordance with a preferred embodiment, the feed is a pyrolysis gasoline. The pyrolysis gasoline corresponds to a cut the boiling point of which is generally in the range 0° C. to 250° C., preferably in the range 10° C. to 220° C. This feed generally comprises the C5-C12 cut with traces of C3, C4, C13, C14, C15 (for example between 0.1% and 3% by weight for each of these cuts).

As an example, a C5-200° C. cut generally has the following composition, as a % by weight:

| | |
|---|---|
| Paraffins | 8-12 |
| Aromatics | 58-62 |
| Monoolefins | 8-10 |
| Diolefins | 18-22 |
| Sulphur | 20-300 ppm |

Selective hydrogenation of a pyrolysis gasoline consists of bringing the feed to be treated into contact with hydrogen introduced in excess into one or more reactors containing the hydrogenation catalyst.

The hydrogen flow rate is adjusted in order to provide a sufficient quantity to theoretically hydrogenate all of the diolefins, acetylenes and alkenyl aromatics and to maintain an excess of hydrogen at the reactor outlet. In order to limit the temperature gradient in the reactor, it may be advantageous to recycle a fraction of the effluent to the inlet and/or to the middle of the reactor.

In the case of the selective hydrogenation of pyrolysis gasoline, the hydrogen/(polyunsaturated compounds to be hydrogenated) molar ratio is generally in the range 1 to 2, the temperature is generally in the range 40° C. to 200° C., preferably in the range 50° C. to 180° C., the hourly space velocity (corresponding to the volume of hydrocarbon per volume of catalyst per hour) is generally in the range 0.5 $h^{-1}$ to 10 $h^{-1}$, preferably in the range 1 $h^{-1}$ to 5 $h^{-1}$, and the pressure is generally in the range 1.0 MPa to 6.5 MPa, preferably in the range 2.0 MPa to 3.5 MPa.

EXAMPLES

The examples presented below are intended to demonstrate the improvement in catalytic activity for selective hydrogenation of the catalysts in accordance with the invention. Examples 1 to 3 and 8 concern processes for the preparation of catalysts which are not in accordance with the invention, and Examples 4 to 7 concern processes for the preparation of a catalyst in accordance with the invention.

Example 9 concerns the application of these catalysts in a selective hydrogenation reaction.

Example 1: Preparation of a Catalyst C1 (not in Accordance with the Invention)

In this example, the specific surface area of the support was lower than that of the catalysts in accordance with the invention (i.e. less than 140 m$^2$/g). Furthermore, the impregnation step was not in accordance with the invention.

A colloidal suspension of Pd oxide was prepared, with stirring at 25° C., by diluting 230 g of a solution of palladium nitrate Pd(NO$_3$)$_2$ containing 8.5% by weight of palladium Pd with approximately 4.8 L of demineralized water, then adding approximately 150 mL of a sodium hydroxide solution in order to obtain a pH of 2.4. The suspension was then diluted with demineralized water to a volume which corresponded to the pore volume of the alumina support, which had a specific surface area of 71 m$^2$/g, shaped into the form of beads. This solution was then impregnated in an impregnation drum at a rotational speed of 6 rotations per minute (rpm) and with a flow rate for the addition of the solution of 22 litres/hour (L/h) onto approximately 10 kg of an alumina. A step for maturation of the impregnated support, before drying, for a period of 20 h was carried out in air in a confined, moist medium. The solid obtained was dried for 16 h at 90° C. in a stream of nitrogen. The catalyst was then calcined in a stream of air for 2 h at 450° C.

The catalyst C1 prepared in this manner comprised 0.19% by weight of palladium with respect to the total catalyst weight.

Characterization of catalyst C1 using a Castaing microprobe showed that 80% of the Pd was distributed over a crust with a thickness of approximately 189 μm.

The sodium was homogeneously distributed with a distribution coefficient R(Na)=0.92.

The apparent dispersion of the palladium of the catalyst C1 was 22%.

Example 2: Preparation of a Catalyst C2 (not in Accordance with the Invention)

In this example, the impregnation step was not in accordance with the invention.

A colloidal suspension of Pd oxide was prepared, with stirring at 25° C., by diluting 230 g of a solution of palladium nitrate Pd(NO$_3$)$_2$ containing 8.5% by weight of palladium Pd with approximately 7.5 L of demineralized water, then adding approximately 150 mL of a sodium hydroxide solution in order to obtain a pH of 2.4. The suspension was then diluted with demineralized water to a volume which corresponded to the pore volume of the alumina support, which had a specific surface area of 140 m$^2$/g, shaped into the form of beads. This solution was then impregnated in an impregnation drum at a rotational speed of 6 rotations per minute (rpm) and with a flow rate for the addition of the solution of 22 litres/hour (L/h) onto approximately 10 kg of an alumina. A step for maturation of the impregnated support, before drying, for a period of 20 h was carried out in air in a confined, moist medium. The solid obtained was dried for 16 h at 90° C. in a stream of nitrogen. The catalyst was then calcined in a stream of air for 2 h at 450° C.

The catalyst C2 prepared in this manner comprised 0.19% by weight of palladium with respect to the total catalyst weight.

Characterization of catalyst C2 using a Castaing microprobe showed that 80% of the Pd was distributed over a crust with a thickness of approximately 150 μm.

The sodium was homogeneously distributed with a distribution coefficient R(Na)=0.92.

The apparent dispersion of the palladium of the catalyst C2 was 26%.

Example 3: Preparation of a Catalyst C3 (not in Accordance with the Invention)

In this example, the specific surface area of the support was lower than that of the catalysts in accordance with the invention (i.e. less than 140 m$^2$/g). However, the impregnation step was in accordance with the invention.

A colloidal suspension of Pd oxide was prepared, with stirring at 25° C., by diluting 230 g of a solution of palladium nitrate Pd(NO$_3$)$_2$ containing 8.5% by weight of palladium Pd with approximately 4.8 L of demineralized water, then adding approximately 150 mL of a sodium hydroxide solution in order to obtain a pH of 2.4. The suspension was then diluted with demineralized water to a volume which corresponded to the pore volume of the alumina support, which had a specific surface area of 71 m$^2$/g, shaped into the form of beads. This solution was then impregnated in an impregnation drum at a rotational speed of 14 rpm and with a flow rate for the addition of the solution of 5.4 L/h onto approximately 10 kg of an alumina. A step for maturation of the impregnated support, before drying, for a period of 20 h was carried out in air in a confined, moist medium. The solid obtained was dried for 16 h at 90° C. in a stream of nitrogen. The catalyst was then calcined in a stream of air for 2 h at 450° C.

The catalyst C3 prepared in this manner comprised 0.19% by weight of palladium with respect to the total catalyst weight.

Characterization of catalyst C3 using a Castaing microprobe showed that 80% of the Pd was distributed over a crust with a thickness of approximately 112 μm.

The sodium was homogeneously distributed with a distribution coefficient R(Na)=0.92.

The apparent dispersion of the palladium of the catalyst C3 was 23%.

Example 4: Preparation of a Catalyst C4, in Accordance with the Invention

In this example, the specific surface area of the support was in accordance with the invention. Furthermore, the impregnation step was in accordance with the invention.

A colloidal suspension of Pd oxide was prepared, with stirring at 25° C., by diluting 230 g of a solution of palladium nitrate Pd(NO$_3$)$_2$ containing 8.5% by weight of palladium Pd with approximately 4.8 L of demineralized water, then adding approximately 150 mL of a sodium hydroxide solution in order to obtain a pH of 2.4. The suspension was then diluted with demineralized water to a volume which corresponded to the pore volume of the alumina support, which had a specific surface area of 210 m$^2$/g, shaped into the form of beads. This solution was then impregnated in an impregnation drum at a rotational speed of 14 rpm and with a flow rate for the addition of the solution of 5.4 L/h onto approximately 10 kg of an alumina. A step for maturation of the impregnated support, before drying, for a period of 20 h was carried out in air in a confined, moist medium. The solid obtained was dried for 16 h at 90° C. in a stream of nitrogen. The catalyst was then calcined in a stream of air for 2 h at 450° C.

The catalyst C4 prepared in this manner comprised 0.19% by weight of palladium with respect to the total catalyst weight.

Characterization of catalyst C4 using a Castaing microprobe showed that 80% of the Pd was distributed over a crust with a thickness of approximately 65 µm.

The sodium was homogeneously distributed with a distribution coefficient R(Na)=0.92.

The apparent dispersion of the palladium of the catalyst C4 was 27%.

Example 5: Preparation of a Catalyst C5, in Accordance with the Invention

In this example, the specific surface area of the support was in accordance with the invention. Furthermore, the impregnation step was in accordance with the invention.

A colloidal suspension of Pd oxide was prepared, with stirring at 25° C., by diluting 230 g of a solution of palladium nitrate $Pd(NO_3)_2$ containing 8.5% by weight of palladium Pd with approximately 7.5 L of demineralized water, then adding approximately 150 mL of a sodium hydroxide solution in order to obtain a pH of 2.4. The suspension was then diluted with demineralized water to a volume which corresponded to the pore volume of the alumina support, which had a specific surface area of 140 $m^2/g$, shaped into the form of beads. This solution was then impregnated in an impregnation drum at a rotational speed of 14 rpm and with a flow rate for the addition of the solution of 5.4 L/h onto approximately 10 kg of an alumina. A step for maturation of the impregnated support, before drying, for a period of 20 h was carried out in air in a confined, moist medium. The solid obtained was dried for 16 h at 90° C. in a stream of nitrogen. The catalyst was then calcined in a stream of air for 2 h at 450° C.

The catalyst C5 prepared in this manner comprised 0.19% by weight of palladium with respect to the total catalyst weight.

Characterization of catalyst C5 using a Castaing microprobe showed that 80% of the Pd was distributed over a crust with a thickness of approximately 93 µm.

The sodium was homogeneously distributed with a distribution coefficient R(Na)=0.92.

The apparent dispersion of the palladium of the catalyst C5 was 21%.

Example 6: Preparation of a Catalyst C6, in Accordance with the Invention

In this example, the specific surface area of the support was in accordance with the invention. Furthermore, the impregnation step was in accordance with the invention.

A colloidal suspension of Pd oxide was prepared, with stirring at 25° C., by diluting 230 g of a solution of palladium nitrate $Pd(NO_3)_2$ containing 8.5% by weight of palladium Pd with approximately 6.2 L of demineralized water, then adding approximately 150 mL of a sodium hydroxide solution in order to obtain a pH of 2.4. The suspension was then diluted with demineralized water to a volume which corresponded to the pore volume of the alumina support, which had a specific surface area of 210 $m^2/g$, shaped into the form of three-lobed extrudates with a mean length in the range 3 to 6 mm. This solution was then impregnated in an impregnation drum at a rotational speed of 14 rpm and with a flow rate for the addition of the solution of 5.4 L/h onto approximately 10 kg of an alumina. A step for maturation of the impregnated support, before drying, for a period of 20 h was carried out in air in a confined, moist medium. The solid obtained was dried for 16 h at 90° C. in a stream of nitrogen. The catalyst was then calcined in a stream of air for 2 h at 450° C.

The catalyst C6 prepared in this manner comprised 0.19% by weight of palladium with respect to the total catalyst weight.

Characterization of catalyst C6 using a Castaing microprobe showed that 80% of the Pd was distributed over a crust with a thickness of approximately 25 µm.

The sodium was homogeneously distributed with a distribution coefficient R(Na)=0.92.

The apparent dispersion of the palladium of the catalyst C6 was 31%.

Example 7: Preparation of a Catalyst C7, in Accordance with the Invention

In this example, the specific surface area of the support was in accordance with the invention. Furthermore, the impregnation step was in accordance with the invention.

A colloidal suspension of Pd oxide was prepared, with stirring at 25° C., by diluting 230 g of a solution of palladium nitrate $Pd(NO_3)_2$ containing 8.5% by weight of palladium Pd with approximately 6.2 L of demineralized water, then adding approximately 150 mL of a sodium hydroxide solution in order to obtain a pH of 2.4. The suspension was then diluted with demineralized water to a volume which corresponded to the pore volume of the alumina support, which had a specific surface area of 200 $m^2/g$ shaped into the form of cylindrical extrudates with a mean length in the range 2 to 4 mm. This solution was then impregnated in an impregnation drum at a rotational speed of 14 rpm and with a flow rate for the addition of the solution of 5.5 L/h onto approximately 10 kg of an alumina. A step for maturation of the impregnated support, before drying, for a period of 20 h was carried out in air in a confined, moist medium. The solid obtained was dried for 16 h at 90° C. in a stream of nitrogen. The catalyst was then calcined in a stream of air for 2 h at 450° C.

The catalyst C7 prepared in this manner comprised 0.19% by weight of palladium with respect to the total catalyst weight.

Characterization of catalyst C7 using a Castaing microprobe showed that 80% of the Pd was distributed over a crust with a thickness of approximately 29 µm.

The sodium was homogeneously distributed with a distribution coefficient R(Na)=0.92.

The apparent dispersion of the palladium of the catalyst C7 was 28%.

Example 9: Preparation of a Catalyst C8 (not in Accordance with the Invention)

In this example, the specific surface area of the support was in accordance with the invention. However, the impregnation step was not in accordance with the invention.

A colloidal suspension of Pd oxide was prepared, with stirring at 25° C., by diluting 230 g of a solution of palladium nitrate $Pd(NO_3)_2$ containing 8.5% by weight of palladium Pd with approximately 6.2 L of demineralized water, then adding approximately 150 mL of a sodium hydroxide solution in order to obtain a pH of 2.4. The suspension was then diluted with demineralized water to a volume which corresponded to the pore volume of the alumina support, which had a specific surface area of 210 m²/g shaped into the form of cylindrical extrudates with a mean length in the range 2 to 4 mm. This solution was then impregnated in an impregnation drum at a rotational speed of 25 rpm and with a flow rate for the addition of the solution of 15 L/h onto approximately 10 kg of an alumina. A step for maturation of the impregnated support, before drying, for a period of 20 h was carried out in air in a confined, moist medium. The solid obtained was dried for 16 h at 90° C. in a stream of nitrogen.

The catalyst was then calcined in a stream of air for 2 h at 450° C.

The catalyst C8 prepared in this manner comprised 0.19% by weight of palladium with respect to the total catalyst weight.

Characterization of catalyst C8 using a Castaing microprobe showed that 80% of the Pd was distributed over a crust with a thickness which was below the detection threshold.

The sodium was homogeneously distributed with a distribution coefficient R(Na)=0.91.

The apparent dispersion of the palladium of the catalyst C8 was 13%.

The results for Examples 1 to 8 are shown in Table 1 below.

TABLE 1

Technical and morphological characteristics of catalysts C1 to C8

| | Rotational speed (rpm) | Impregnation solution addition rate (L/h) | $S_{BET}$ support (m²/g) | Shape | Crust size (μm) | Dispersion (%) |
|---|---|---|---|---|---|---|
| C1 (not in accordance) | 6 | 22 | 71 | beads | 189 | 22 |
| C2 (not in accordance) | 6 | 22 | 140 | beads | 150 | 26 |
| C3 (not in accordance) | 14 | 5.4 | 71 | beads | 112 | 23 |
| C4 (in accordance) | 14 | 5.4 | 210 | beads | 65 | 27 |
| C5 (in accordance) | 14 | 5.4 | 140 | beads | 93 | 21 |
| C6 (in accordance) | 14 | 5.4 | 210 | three-lobed extrudates | 25 | 31 |
| C7 (in accordance) | 14 | 5.5 | 200 | cylindrical extrudates | 29 | 28 |
| C8 (not in accordance) | 25 | 15 | 210 | cylindrical extrudates | <dt* | 13 |

*dt = detection threshold

Example 9: Use of Catalysts C1 to C8 for the Selective Hydrogenation of a Steam Cracked Pygas Cut Testing the catalytic hydrogenation of a styrene-isoprene mixture in the presence of S.

Before the catalytic test, the catalysts C1 to C8 were treated in a stream of 1 litre of hydrogen per hour and per gram of catalyst with a temperature ramp-up of 300° C./h and a constant temperature stage at 150° C. for 2 hours.

The catalysts then underwent a hydrogenation test in a continuously stirred "Grignard" type batch reactor. To this end, 4 mL of beads or extrudates of reduced catalyst were fixed, with the exclusion of air, in an annular basket located around the stirring blade. The baskets used in the reactors were of the Robinson Mahonnay type.

Hydrogenation was carried out in the liquid phase.

The composition of the feed was as follows: 8% by weight of styrene, 8% by weight of isoprene, 10 ppm of S introduced in the form of pentanethiol, 100 ppm of S introduced in the form of thiophene, the solvent being n-heptane.

The test was carried out under a constant pressure of 3.5 MPa of hydrogen and at a temperature of 45° C. The reaction products were analysed by gas phase chromatography.

The catalytic activities are expressed in moles of $H_2$ consumed per minute and per gram of palladium and are reported in Table 2 below.

TABLE 2

Activities measured for the hydrogenation of a styrene-isoprene mixture in the presence of sulphur

| Catalyst | Activity* | %/Ref** |
|---|---|---|
| C1 (not in accordance) | 0.31 | 41 |
| C2 (not in accordance) | 0.63 | 84 |
| C3 (not in accordance) | 0.52 | 69 |
| C4 (in accordance) | 0.75 | 100 |
| C5 (in accordance) | 0.73 | 97 |
| C6 (in accordance) | 1.13 | 150 |
| C7 (in accordance) | 0.97 | 130 |
| C8 (not in accordance) | 0.59 | 79 |

*in (moles $H_2$)/[min × (grams of palladium)]
**%/Ref corresponds to the gain converted into a % obtained with respect to the reference catalyst C4 for which the activity was defined as 100%.

It will be observed that the catalysts C4, C5, C6 and C7 had a higher activity compared with catalysts C1, C2, C3 and C8 (not in accordance with the invention).

The catalyst C8 had a crust thickness which was too thin (<20 μm) because of the high specific surface area of its support and because the preparation process was unsuitable (the revolving drum rotated too fast, and also the flow rate was too high).

Catalyst C1 did not produce satisfactory results in terms of activity because it had been prepared by a process which was not in accordance with the invention. Furthermore, the catalyst C1 had a specific surface area which was too low.

The catalyst C2 did not produce satisfactory results in terms of activity because it had been prepared by a process which was not in accordance with the invention.

The catalyst C3 did not produce satisfactory results in terms of activity, even though the step for impregnation of the colloidal solution onto the support was in accordance with the invention because it had been prepared using a support with a specific surface area which was too low.

BRIEF DESCRIPTION OF THE FIGURES

FIG. 1 is a cross-section of an extrudate in a plane perpendicular to the direction of extrusion.

The invention claimed is:

1. A process for the preparation of a catalyst comprising palladium, a porous support comprising at least one refractory oxide selected from the group consisting of silica, alumina and silica-alumina, said porous support having a specific surface area of 140 to 250 m²/g, wherein at least 80% by weight of the palladium is distributed in a crust at the periphery of said support, the thickness of said crust being 20 to 100 μm, said process comprising:
   a) preparing a colloidal solution of palladium oxide or palladium hydroxide in an aqueous phase;
   b) adding said solution obtained from step a) to said porous support at a flow rate of 1 to 20 liter(s)/hour;

said porous support being contained in a rotary impregnation device functioning at a rotational speed of 10 to 20 rpm;

c) optionally, submitting the impregnated porous support obtained from step b) to a maturation in order to obtain a catalyst precursor;

d) drying the catalyst precursor obtained from step b) or c) at a temperature of 70° C. to 200° C.;

e) calcining the catalyst precursor obtained from step d) at a temperature of 300° C. to 500° C.

2. The process as claimed in claim 1, wherein said porous support is in the form of a bead.

3. The process as claimed in claim 1, wherein said porous support is in the form of an extrudate.

4. The process as claimed in claim 3, wherein said porous support is in the form of an extrudate with a length h of 2 to 10 mm.

5. The process as claimed in claim 3, wherein said porous support comprises a section comprising at least three lobes.

6. The process as claimed in claim 5, wherein the number of lobes of the extrudate, n, is an integer 3, 4, 5, 6, 7, 8, 9 or 10.

7. The process as claimed in claim 6, wherein the number of lobes of the extrudate, n, is an integer 4, 5, 6, 7, 8, 9 or 10.

8. The process as claimed in claim 5, wherein the number of lobes, n, is an integer 3 or 4.

9. The process as claimed in claim 3, wherein the extrudate is in the form of a cylinder.

10. The process as claimed in claim 1, wherein the palladium content in the catalyst is 0.01% to 2% by weight with respect to the total catalyst weight.

11. The process as claimed in claim 1, wherein said catalyst further comprises silver at a content of 0.02% to 3% by weight of silver with respect to the total catalyst weight.

12. The process as claimed in claim 1, wherein the metallic dispersion D of the palladium is 15% to 70%.

13. The process as claimed in claim 1, wherein the support has a pore diameter of 2 to 50 nm.

14. The process as claimed in claim 1, wherein a maturation step c) is carried out for a period of 0.5 to 40 hours.

15. The process as claimed in claim 1, wherein said dried catalyst obtained from step e) undergoes a reduction treatment by contact with a reducing gas at a temperature of 80° C. to 180° C.

16. The process as claimed in claim 1, wherein the rotary impregnation device of step b) is a revolving drum.

17. The process as claimed in claim 1, wherein the process results in palladium crust size of 20 to 100 μm.

18. The process as claimed in claim 1, wherein the process results in a catalyst with an activity of at least 0.75 (moles $H_2$)/[min×(grams of palladium) as measured for the hydrogenation of a styrene-isoprene mixture in the presence of Sulphur.

* * * * *